(12) United States Patent
Kliegman et al.

(10) Patent No.: US 12,366,674 B2
(45) Date of Patent: Jul. 22, 2025

(54) IN-VEHICLE OCCUPANT SAFETY MONITORING SYSTEMS AND METHODS

(71) Applicant: Zeteo Tech, Inc., Sykesville, MD (US)

(72) Inventors: Ross Kliegman, Sykesville, MD (US); Lara Moore, Sykesville, MD (US); Jonathan Nusbaum, Sykesville, MD (US); Wayne A. Bryden, Sykesville, MD (US); Thomas McCreery, Sykesville, MD (US)

(73) Assignee: Zeteo Tech, Inc., Sykesville, MD (US)

( * ) Notice: Subject to any disclaimer, the term of this patent is extended or adjusted under 35 U.S.C. 154(b) by 346 days.

(21) Appl. No.: 18/107,783

(22) Filed: Feb. 9, 2023

(65) Prior Publication Data

US 2024/0272319 A1     Aug. 15, 2024

(51) Int. Cl.
| | |
|---|---|
| *G01N 33/00* | (2006.01) |
| *G01J 5/00* | (2022.01) |
| *G01V 1/00* | (2006.01) |
| *G01V 1/18* | (2006.01) |
| *B60R 11/00* | (2006.01) |

(52) U.S. Cl.
CPC ............ *G01V 1/001* (2013.01); *G01J 5/0025* (2013.01); *G01N 33/004* (2013.01); *G01V 1/181* (2013.01); *B60R 2011/0049* (2013.01)

(58) Field of Classification Search
CPC ....... G01V 1/001; G01V 1/181; G01J 5/0025; G01N 33/004; B60R 2011/0049
See application file for complete search history.

(56) References Cited

U.S. PATENT DOCUMENTS

| | | | | |
|---|---|---|---|---|
| 4,096,474 A | * | 6/1978 | Greer ................. | G08B 13/1663 367/136 |
| 4,415,979 A | * | 11/1983 | Hernandez ............. | G08B 13/00 367/136 |
| 6,222,442 B1 | * | 4/2001 | Gager ..................... | E05B 83/16 70/92 |
| 6,370,481 B1 | * | 4/2002 | Gamble ................. | G01V 1/001 702/56 |
| 7,472,554 B2 | | 1/2009 | Vosburgh | |
| 8,212,665 B2 | | 7/2012 | Schoenberg et al. | |
| 8,258,932 B2 | | 9/2012 | Wahlstrom | |
| 9,227,484 B1 | | 1/2016 | Justice et al. | |
| 2005/0038582 A1 | | 2/2005 | Arndt et al. | |

(Continued)

OTHER PUBLICATIONS

Ranta, R. et al., "Detection of human presence in a vehicle by vibration analysis," IET Intelligent Transport Systems, Dec. 2012.

(Continued)

*Primary Examiner* — Freddie Kirkland, III
(74) *Attorney, Agent, or Firm* — Paradice and Li LLP; Anand S. Chellappa

(57) ABSTRACT

In-vehicle occupant detection system and methods capable of monitoring the interior of a passenger vehicle and responding to potentially dangerous situations are disclosed. The detection systems may comprise a front camera to focus on driver and passenger behavior in the front cabin, and a rear camera and an array of environmental sensors to detect unattended occupants including children, adults or pets in the rear seats. Data may be processed by an intelligent algorithm to assesses anomalies and trigger one or more alarms or countermeasures.

21 Claims, 12 Drawing Sheets

(56) References Cited

U.S. PATENT DOCUMENTS

| | | |
|---|---|---|
| 2007/0025597 A1* | 2/2007 | Breed ................ B60N 2/0033 |
| | | 382/104 |
| 2014/0278145 A1 | 9/2014 | Angeli et al. |
| 2014/0365100 A1 | 12/2014 | Speier |
| 2016/0096412 A1 | 4/2016 | Mankame et al. |
| 2016/0103111 A1 | 4/2016 | Griffin |
| 2023/0419690 A1 | 12/2023 | Tong et al. |

OTHER PUBLICATIONS

"In-Vehicle Occupant Detection System," publication by Zeteo Tech Inc. on its website, Nov. 16, 2021.

\* cited by examiner

| Dangerous Condition | Response 1 | Response 2 | Response 3 |
|---|---|---|---|
| Improper interior settings | Voice notification | Lockout of starting vehicle | Communication to list |
| Seat belt nonuse/misuse | Voice notification | Lockout of starting vehicle | |
| Unsafe occupant position | Voice notification | Lockout of starting vehicle | |
| Drowsy driver | Audible alert | Communication to list | |
| Impaired driver | Voice notification | Lockout of starting vehicle | Communication to authorities (911) |
| Distracted driver | Voice notification | Communication to list | |
| Medical condition | Voice notification to passengers | Communication to list | Communication to authorities (911) |
| Unattended children | Communication to list | Communication to authorities (911) | Sound car alarm, Cooling measures, others |

FIG. 5

| Weight (kg) | Tidal Volume (L) | Breaths/min | V/min (L) | $CO_2$/min (L) | 1 hr Peak $CO_2$ | Small Car |
|---|---|---|---|---|---|---|
| 5 | 0.04 | 45 | 1.6 | 0.063 | 440 ppm | 880 ppm |
| 10 | 0.07 | 30 | 2.1 | 0.084 | 580 ppm | 1160 ppm |
| 25 | 0.18 | 25 | 4.5 | 0.18 | 1250 ppm | 2500 ppm |
| 45 | 0.32 | 20 | 6.4 | 0.26 | 1800 ppm | 3600 ppm |
| 75 | 0.52 | 15 | 7.8 | 0.31 | 2200 ppm | 4400 ppm |
| 100 | 0.70 | 15 | 10.5 | 0.42 | 2900 ppm | 5800 ppm |

FIG. 7

IN-VEHICLE OCCUPANT SAFETY MONITORING SYSTEMS AND METHODS

FIELD

This disclosure relates to in-vehicle passenger safety monitoring systems and methods to detect one or more anomalies caused by one or more of drowsy driving, distracted driving, or improper seat-belt use, or due to an unattended person left in a parked vehicle. More particularly, but not by way of limitation, the present disclosure relates to systems and methods for detecting the presence of an unattended child or pet in a vehicle.

BACKGROUND

Vehicle-related tragedies are often the result of preventable behaviors like drowsy driving, distracted driving, and leaving children unattended in cars. These actions have dramatic consequences, causing the death of about 50 children per year left in hot cars, and thousands of people to die from drowsy and distracted driving. The ability to monitor the inside of a passenger vehicle can provide positive safety impacts. A monitoring system may provide critical information about the safety of the passengers in the vehicle, including, the presence of occupant(s), presence of unattended children, seat belt (non)-use, misuse, occupants in unsafe positions such as having their leg on the dashboard, drowsy or impaired drivers, distracted drivers, and drivers impacted by a medical condition. High priority safety concerns may include detecting distracted drivers, detecting drowsy drivers, and detecting unattended persons, passengers, or children left in hot (or cold) cars.

Statistics from the U.S. National Highway Traffic Safety Administration show that about 9% of fatal crashes in 2017 were reported as distraction-affected crashes. These crashes killed 3,166 people directly and killed another 599 nonoccupants comprising pedestrians, bicyclists, and others. Despite public education efforts, the number of deaths and the percentage of total fatal crashes involving distracted driving has remained virtually unchanged since 2013, with approximately 3,000 fatalities resulting from about 9% of fatal crashes. Clearly, better approaches aimed at detecting and deterring this behavior have the potential to reduce the number of preventable deaths. Further, drowsy driving is a significant cause of highway deaths. The U.S. Center for Disease Control and Prevention reported that 4.2% of drivers surveyed reported having fallen asleep within the last 30 days before the survey. Despite education and other efforts, the number of fatal crashes involving drowsy drivers remained virtually unchanged for many years, and trends from 2011-2015 remained roughly constant from year to year.

Heat stroke deaths in children left unattended in hot cars are avoidable tragedies that occur far too often in the United States, particularly in the warmer months of the year. On average, about 39 children under the age of 15 years die every year. The number of hot car deaths has increased in recent years, with 53 deaths in 2018 and 52 deaths in 2019. Since 1998, about 849 children left unattended in hot cars were killed by heat stroke, with deaths reported in every state except Alaska, Vermont, and New Hampshire. These accidental deaths may occur due to a variety of reasons. For example, an unexpected change in routine driving may cause a parent or caretaker to leave the child in the car. Another cause is termed as "autopilot" by the National Safety Council where a parent who does not normally have the child in his/her vehicle forgets to drop off his/her child at day care, but instead drives to work or to the gymnasium without realizing that the child is left unattended in the car. Distraction can also be a key factor in a child being left unattended in a car. Quite heartbreakingly, exhausted new parents often do not recall leaving their child unattended in a car simply due to lack of sleep.

Current safety products include smart clips that alert the parent if his/her child was not removed from the car seat (Evenflo), a weight sensor that may be disposed under the padding in a car seat (Driver's Little Helper Sensor System), a setting on the Waze navigation application software or "app" (Google) to remind drivers to check the back seat, and the General Motors Rear Seat Reminder System that reminds drivers to check the back seat when the rear passenger doors are opened and closed within 10 minutes of the vehicle going into motion. Tesla Model S cars offer two safety modes, namely, (1) dog mode, which keeps pets comfortable while also displaying the current cabin temperature on a touchscreen so that people nearby and looking into the car are informed that the pet does not need to be rescued, (2) a cabin overheat protection mode, whereby the climate control system can reduce the temperature of the cabin in extremely hot ambient conditions for a period of up to twelve hours after the driver exits the car. These modes are not helpful for keeping children safe because if the driver remembers to implement the cooling mode before exiting the vehicle, he/she will surely remember to take his/her child out of the car before exiting. Time is of the essence because the temperature inside a car parked in the sun on a hot day can rise to deadly temperatures (>40° C.) within a matter of minutes.

None of the commercially available products and methods directly monitors the presence of a vehicle occupant who is left unattended in a vehicle. For example, current systems check how many times each vehicle door has been opened and closed and infer if a child is left in the car based on the number of opening/closing of each door. This door-based logic can be bypassed and even disabled. Systems and methods for autonomously detecting the presence of children and pets in unattended vehicles and to provide a series of measures to counter unsafe driving behavior are needed. Systems and methods for unattended vehicle occupant detection with extremely low false alarm (positive) rates are needed.

BRIEF DISCLOSURE

Disclosed is an example system for detecting the presence of an unattended occupant inside a vehicle. The example system may include a geophone vibration sensor configured to continuously sample at a predetermined sampling rate the vibration produced by the vehicle and output a geophone sensor voltage signal, a cabin temperature sensor configured to continuously sample at a predetermined sampling rate the temperature within the vehicle and output a temperature sensor signal, a cabin carbon dioxide ($CO_2$) sensor configured to continuously sample at a predetermined sampling rate the $CO_2$ levels within the vehicle and output a $CO_2$ sensor signal, and a controller disposed in communication with the geophone vibration sensor, the cabin temperature sensor, and the cabin carbon dioxide sensor. The controller may be configured to trigger a safety protocol to determine the presence of an unattended occupant when the voltage difference ($\Delta V$) between the exponential moving average of a predetermined number of data points of the geophone sensor voltage signal at time ($t_n$) and at a previous time ($t_{n-1}$)

is less than or equal to a predetermined ΔV threshold. The time $t_{n-1}$ indicates any time previous to $t_n$. The predetermined number of data points of the geophone sensor voltage signal may be between 2 and 10. The predetermined ΔV threshold may be less than or equal to about 0.1 V. The system may further include a thermal imaging camera configured to monitor the rear cabin of the vehicle at a predetermined frame rate. The predetermined frame rate may be about 9 Hz. The thermal imaging camera may be characterized by a field of view of at least 95 degrees. The example system may further comprise one or more of a PIR motion sensor or a sound sensor. The PIR motion sensor may be configured to continuously sample at a predetermined sampling rate an occupant movement (movement of an occupant, in particular, an unattended occupant like child or pet) within the vehicle. The sound sensor may be configured to continuously sample at a predetermined sampling rate an occupant sound (the sound made by an occupant) within the vehicle.

In some implementations of the example system, the controller may be further configured to turn on the thermal imaging camera or monitor a signal from the PIR motion sensor or monitor a signal from the sound sensor, or a combination thereof, if the temperature sensor signal indicates the cabin temperature to be below about 10° C. or above about 30° C. or the exponential moving average of $CO_2$ level rate of change calculated using the $CO_2$ sensor signal is at least about 0.2 ppm/s. The predetermined sampling rate for one or more of the geophone sensor or temperature sensor may be about 10 Hz. The predetermined sampling rate for the $CO_2$ sensor may be about 0.2 Hz. The controller may be further configured to communicate with a remote server to capture and process one or more of the geophone vibration sensor voltage signal, the temperature sensor signal, the $CO_2$ sensor signal, or a plurality of images captured using the thermal imaging camera. The example system may be further configured to communicate with an app.

Disclosed is an example system for detecting the presence of an unattended occupant inside a vehicle. The system may include a transponder unit including a plurality of sensors configured to monitor environmental conditions inside the vehicle and a receiver unit, which may be disposed in bidirectional data communication with the transponder unit. The receiver unit may comprise a geophone vibration sensor configured to continuously sample at a predetermined data rate the vibration produced by the vehicle and output a geophone sensor voltage signal and a controller. The controller may be configured to trigger a safety protocol if the voltage difference (ΔV) between the exponential moving average of a predetermined number of data points of the geophone sensor voltage signal at time ($t_n$) and at a previous time ($t_{n-1}$) is less than or equal to a predetermined ΔV threshold. The time $t_{n-1}$ indicates any time previous to $t_n$. The predetermined number of data points of the geophone sensor voltage signal may be between 2 and 10. The predetermined ΔV threshold may be less than or equal to about 0.1 V. The plurality of sensors in the transponder unit may include one or more of a temperature sensor, a $CO_2$ sensor, a PIR motion sensor, or a sound sensor. The transponder may further include a thermal imaging camera. The transponder unit may be configured to be removably disposed in one or more of a ceiling of the vehicle or a grab handle disposed above a rear seat of the vehicle. The transponder unit may further include a rechargeable battery. The receiver unit further may include a rechargeable battery. The transponder unit and receiver unit may be configured to wirelessly communicate with each other.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawings, wherein:

FIG. 1 shows a schematic diagram of an example in-vehicle passenger detection system architecture, according to some implementations.

FIG. 2A-B show perspective views of an example passenger detection system with sensors integrated in a single package, according to some implementations.

FIG. 5 shows a summary of example safety system response options and hierarchy, according to some implementations.

FIG. 7 shows a summary of example $CO_2$ levels for triggering an alarm for detecting an unattended person in a parked vehicle, according to some implementations.

Figure 8A:
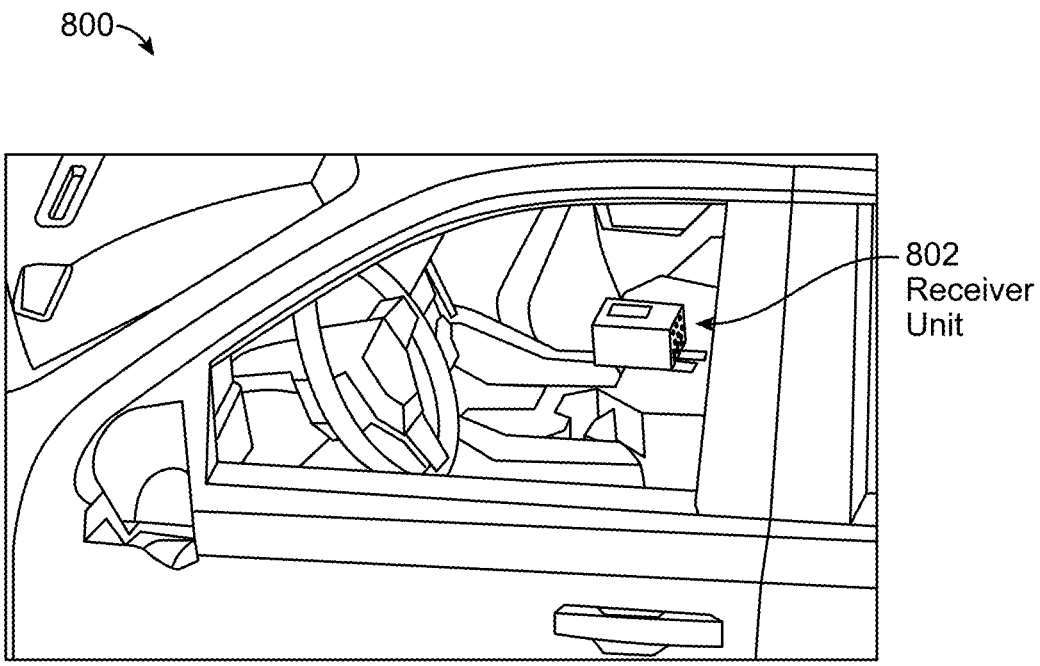
Figure 8B:
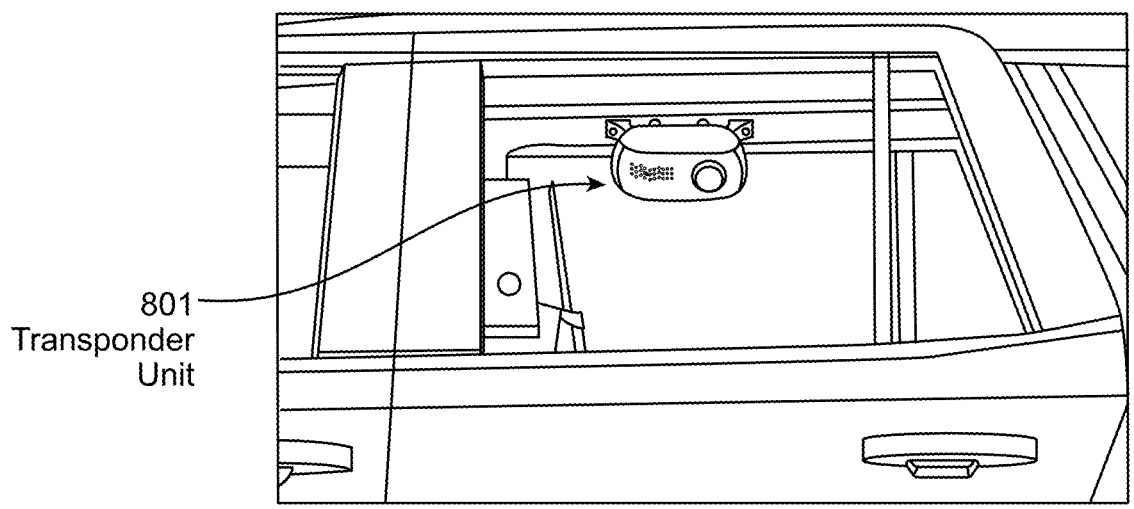

FIGS. 8A-B show schematic diagrams of an example receiver (A) and transponder (B) of an example in-vehicle passenger safety monitoring system showing example locations inside a vehicle, according to some implementations.

Figure 9A:
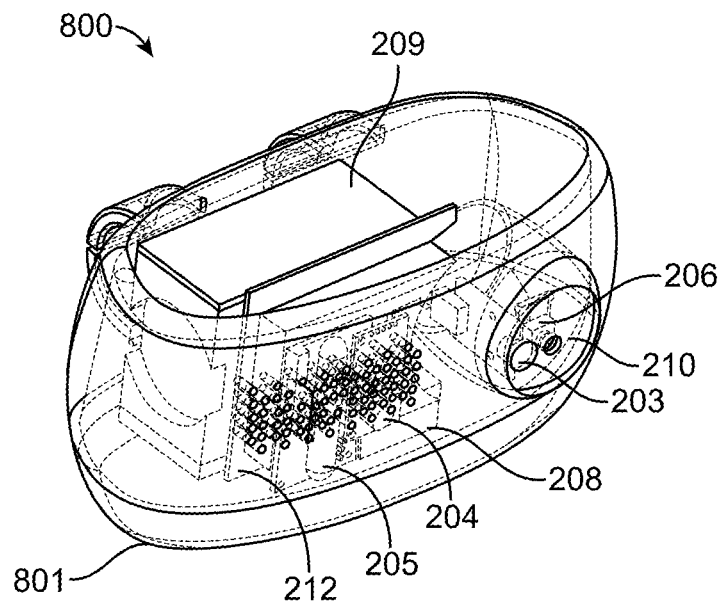
Figure 9B:
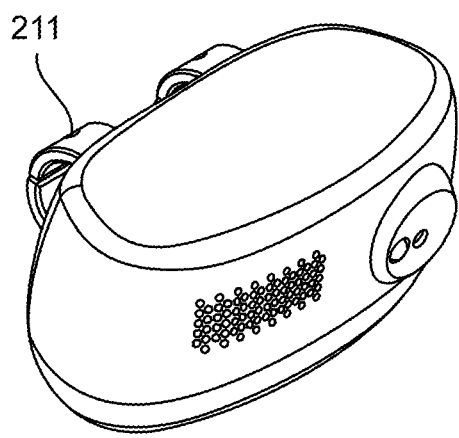
Figure 9C:
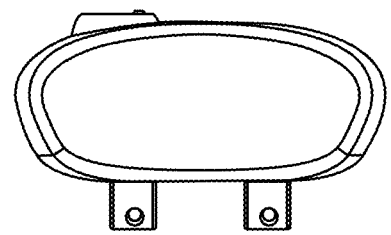

FIGS. 9A-C show perspective views of an example transponder unit of an in-vehicle unattended person detection system, (A) showing internal components, (B) side view and (C) top view, according to some implementations.

Figure 10A:
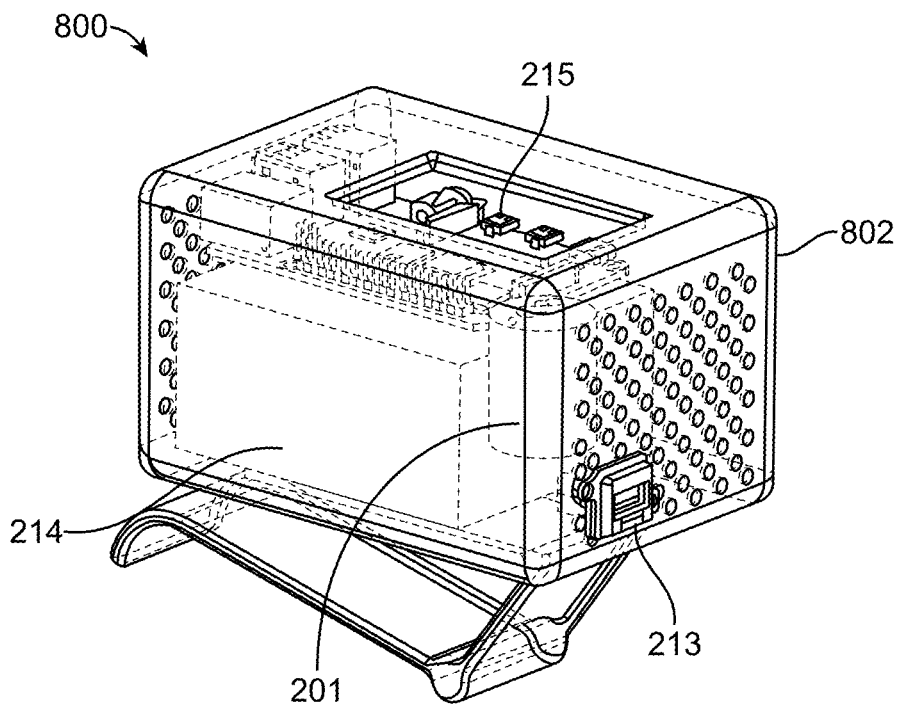
Figure 10B:
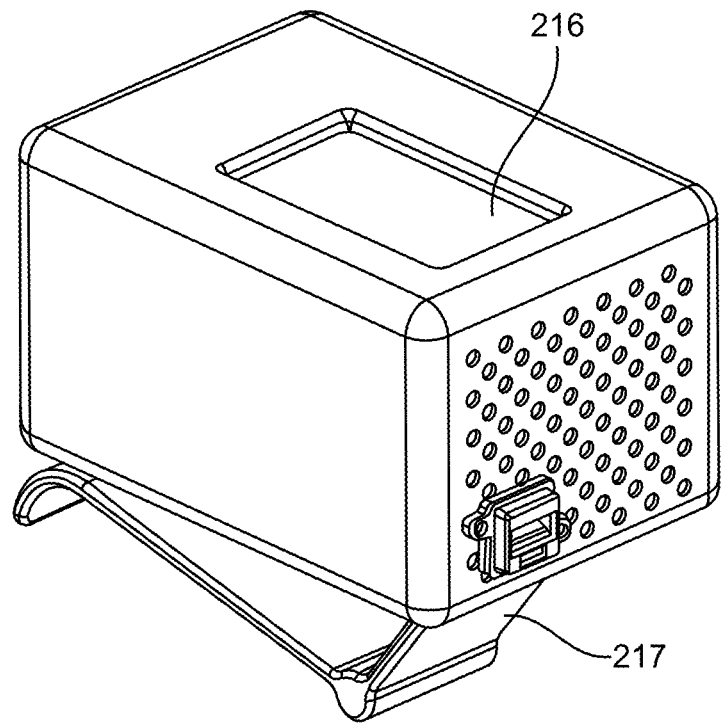

FIGS. 10A-B show perspective views of an example receiver unit of an in-vehicle unattended person detection system, (A) showing internal components, (B) showing an LCD display screen, according to some implementations.

Figure 11:
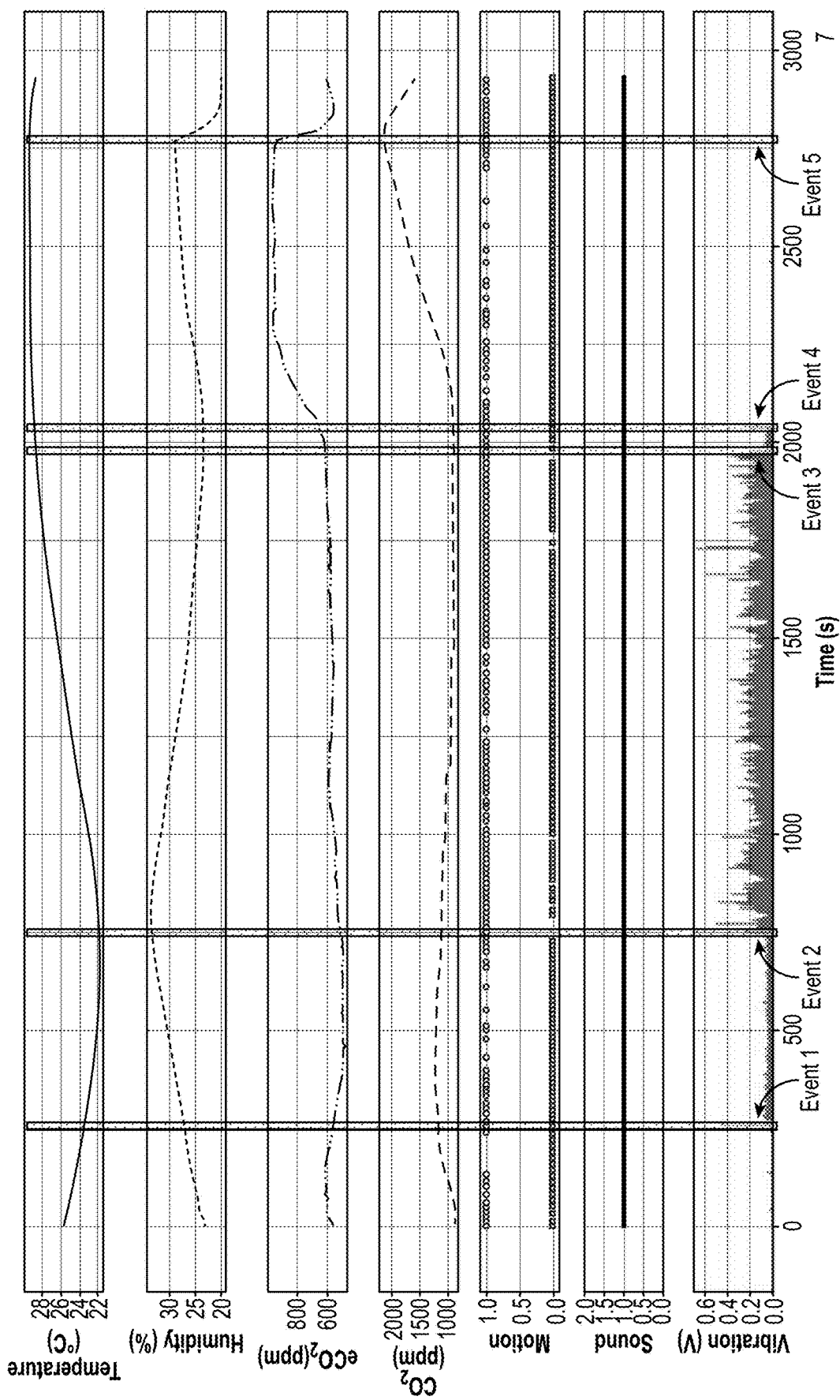

FIG. 11 shows an output of sensors in example system 200 during various events related to starting, driving, and stopping a car, according to some implementations.

Like reference numbers and designations in the various drawings indicate like elements. All reference numerals, designators and callouts in the figures are hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawings show, by way of illustration, specific embodiments in which the disclosed systems and methods may be practiced. These embodiments, which are to be understood as "examples" or "options," are described in enough detail to enable those skilled in the art to practice the present invention. The embodiments may be combined, other embodiments may be utilized, or structural or logical changes may be made, without departing from the scope of the invention. The following detailed description is, therefore, not to be taken in a limiting sense and the scope of the invention is defined by the appended claims and their legal equivalents.

The terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. Unless otherwise specified in this disclosure, for construing the scope of the term "about," the error bounds associated with the values (dimensions, operating conditions etc.) disclosed is ±10% of the values indicated in this disclosure. The error bounds associated with the values disclosed as percentages is ±1% of the percentages indicated. The word "substantially" used before a specific word includes the meanings "considerable in extent to that which is specified." and "largely but not wholly that which is specified." The word "autonomously" means "with no intervention by a human."

DETAILED DISCLOSURE

The following description is directed to some example implementations for the purpose of describing innovative aspects of this disclosure. However, a person having ordinary skill in the art will readily recognize that the teachings herein can be applied in a multitude of different ways. As such, the disclosed implementations are not to be limited by the examples provided herein, but rather encompass all implementations contemplated by the attached claims. Additionally, well-known elements of the disclosure will not be described in detail or will be omitted so as not to obscure the relevant details of the disclosure. Particular aspects of the invention are described below in considerable detail to illustrate compositions, principles, and operations of the disclosed methods and systems. However, various modifications may be made, and the scope of the invention is not limited to the example aspects described.

Disclosed are example detection systems and methods for detecting unattended children or pets, in vehicles and to avoid death due to dangerous heatstroke conditions. The disclosed systems and methods may also substantially reduce the incidence of drowsy driving, distracted driving, unsafe driving (e.g., improper seat-belt use) and the death rate from these types of accidents. The example systems and methods may be configured to execute a series of countermeasures with increasing severity while complying with local laws and regulations. Example countermeasures may include one or more of communicating with designated contact persons by text or phone, calling 911 or other emergency services, lowering the car windows, or starting the car air conditioning system or cabin climate control system. Since these countermeasures could raise significant negative consequences in the event of a false detection or alarm, low false alarm rates are targeted by employing a detection system that is configured to provide multiple independent data streams from various sensors for analysis. In some example implementations, the disclosed detection systems and methods with an "alert hierarchy" may employ image processing collected from one or more digital cameras and artificial intelligence/machine learning (AI/ML) methods, including deep learning models for image classification, to monitor the interior of an unattended vehicle.

Disclosed is an example in-vehicle unattended person detection system 100 (FIG. 1) that include a plurality of sensors, which may interface with processor 107, which may include an Arduino microcontroller, Raspberry Pi microcontroller or similar microcontrollers. System 100 may include a geophone vibration sensor 101 to detect the motion of a vehicle by monitoring the vibration of the vehicle. System 100 may be used for detecting unattended children in vehicles. Geophone sensor 101 may be configured to detect whether a vehicle is in motion based on the magnitude of the vibration of the vehicle. Sufficiently large vibration may suggest that a vehicle is in motion. As such, the location of the geophone sensor inside the vehicle is not important. Other alternatives to a geophone vibration sensor for detecting whether a car is in motion may include one or more location sensors 102, which may include a digital compass, a GPS system, or an accelerometer. An inertial measurement unit or motion tracking sensor (TDK, Model ICM-20948), which provides nine degrees of freedom (a 3-axis gyroscope, a 3-axis accelerometer, and a 3-axis compass) may also be used as a location sensor. To determine whether a car is in motion, dedicating one channel of this sensor for the digital compass/magnetometer may be sufficient. While the compass/magnetometer may provide accurate information related to vehicular motion, a geophone sensor 101 is a simpler type of motion/vibration sensor comprising of only a magnet suspended in a coil of wire. Example geophone sensor 101 (SM-24, Sensor Nederland, b.v.) may be configured to translate ground movement into voltage, that may be converted to a digital signal using an analog to digital converter and fed to processor 107. Geophone sensor 101 requires no bias voltage, is very sensitive to vibration, and produces a strong signal. The signal amplitude of geophone sensor 101 increases when the car engine is turned on and decreases when the engine is turned off, suggesting that that the geophone sensor 101 is sensitive enough to discern whether the car is parked with engine on or whether the car is in motion.

Example unattended occupant detection system 100 may also comprise a temperature sensor 102 to measure the temperature inside the vehicle. The heat index combination of temperature and relative humidity within a vehicle provides system 100 may provide critical safety information related to the passenger compartment or cabin. Furthermore, while the reported deaths associated with unattended occupants of a vehicle are primarily due to hot temperatures, there is the potential for unattended occupants to be injured or killed in freezing temperatures. Example sensors for temperature and humidity may include an integrated (or augmented) temperature/relative humidity sensor 108 such as one or more of DHT22 (Gear box Labs) or solid-state temperature/relative humidity sensor (Bosch, Model BME280), which may digitally interface with a suitable microcontroller such the Arduino, Raspberry Pi, or other suitable microcontrollers. The Bosch integrated temperature/RH sensor 108 may comprise an air quality sensor that may be run with Bosch Sensortec Environmental Cluster (BSEC) algorithm to capture raw data and calculate equivalent air-quality, temperature, relative humidity and atmospheric pressure values. Integrated sensor 108 may also be calibrated to indirectly calculate or estimate equivalent $CO_2$ levels ($eCO_2$) using detected levels of hydrogen, hydrocarbons, and other volatile organic gases along with humidity (RH). Calculated data may be output using a USB connector in different configurable formats (JSON, CSV, human readable or binary). Sensor 108 may be configured to detect a range of gases including volatile organic compounds and also detect temperature, barometric pressure, and relative humidity.

While millions of cars or vehicles may get dangerously hot (or cold) while parked every day, it is critical to unambiguously determine if there is an unattended occupant in a tiny fraction of those parked cars. Because of the large number of cars, the false alarm rate of detection system 100 should be very low to differentiate from a response analogous to normal "car alarms." Typical car alarm systems are subject to false-alarms frequently and as a result, most car alarms are largely ignored with no response taken. To avoid this lack of response in an unattended passenger in a parked car situation, multiple independent sensors may be needed to provide independent data streams representative of occupancy information. For example, a rear camera module with image analysis may be used to confirm unattended vehicle occupancy. Another alternative would be measuring body temperature of an occupant in the rear cabin of the vehicle, for example using a temperature sensor appropriately disposed in a car seat to sense if a child is strapped into a car seat. However, given the requirement to avoid false alarms and the potential for children or pets to be out of the line-of-sight of a camera, sensor options that do not rely on cameras may include monitoring $CO_2$ levels within the cabin of a parked car. A rise in $CO_2$ concentration from exhaled breath in an enclosed cabin may be another indicator of an unattended person in a parked vehicle as exhaled breath from humans comprises about 4% $CO_2$.

In addition to false alarms, system 100 may also be characterized by low false negative detection/alarm rates related to missing the detection of a child trapped in a hot car. System 100 may be characterized by high sensitivity and low false alarm rates, although there is a tradeoff between these two performance-metrics. This tradeoff can be visualized in a ROC curve (receiver operating characteristic curve, plot of sensitivity vs. false alarm rate for a variety of thresholds), which may be used to select various sensor threshold settings. As such, false alarm rate may be set to achieve an associated sensitivity of nearly 100%. For example, detection system 100 may be characterized by approximately one false alarm per year.

Very low false alarm rates are targeted so that alarms from system 100 are not ignored. As previously described, low false alarm rates are achieved by using multiple sensors/data streams, each having its own threshold to answer a "yes/no" question related to unattended occupant detection in a vehicle. For example, in the case of the $CO_2$ sensor 105, a probable "yes/no" question is whether or not the $CO_2$ concentration is increasing. This question is addressed by comparing a measurement of the recent change in $CO_2$ concentration over a time interval with a threshold change in $CO_2$ concentration. A similar threshold may apply to each sensor, and collectively, these thresholds may be used to determine how often the algorithm that runs system 100 declares an alarm. The lower these thresholds, the higher the sensitivity to real threats but also the higher the false positive rate. Conversely, the higher these thresholds, the lower the false alarm rate but also the lower the sensitivity to real threats. As such, each threshold can affect the true and false positive rates. Since a warning or alarm is issued by system 100 first in the form of a text and only in temperature critical situations is 911 (EMS, emergency medical service) called, a false alarm rate of 5% or less may be acceptable for detecting an unattended occupant in a vehicle.

A low-cost sensor to accurately monitor $CO_2$ concentration is critical to realize low false alarm rates in example system 100. Example $CO_2$ sensors 105 may include one or more of an NDIR sensor (Model MH-Z14A, Winsen Sensors) or COZIR-AX-1 (Gas Sensing Solutions). $CO_2$ sensor 105 may also include an infrared carbon dioxide sensor, which may be calibrated for various $CO_2$ ranges (e.g., DFRobot, Gravity PWM infrared $CO_2$ sensor). An example $CO_2$ range may comprise from about 400 ppm to about 5000 ppm. Since $CO_2$ content in ambient air ranges from about 300 ppm to about 400 ppm, the example $CO_2$ sensor may be configured to measure any increase in $CO_2$ due to exhaled breath from an occupant inside a vehicle. Since $CO_2$ disperses in air rapidly, the location of the $CO_2$ sensor in the cabin may not be critical to obtain an accurate $CO_2$ concentration indication or rate of increase in $CO_2$ concentration within the cabin of a parked vehicle. For example, a test array of stand-alone $CO_2$ sensors was constructed for deployment at multiple locations within a 2013 Chevrolet Suburban test sports utility vehicle (SUV). Eight sensors were deployed roughly equidistantly throughout the vehicle, one on each side of the dashboard, one in the center console between the front seats, one on the dome light above the middle seat, one on the floor in front of the middle seat, two on cup holders at the third seat position, and finally one on the floor in the very rear of the vehicle. A human subject was seated in the middle row on the passenger side of the large SUV. After equilibrating the car with the atmosphere and acquiring background data, the subject entered the vehicle, and the doors were closed. The subject remained in the vehicle (parked in the shade) for about 60 minutes. During this time, the subject sat calmly, breathing naturally. All of the sensors showed roughly the same behavior, independent of their position relative to the test subject, suggesting that $CO_2$ disperses rapidly on the order of a few seconds.

Figure 1:
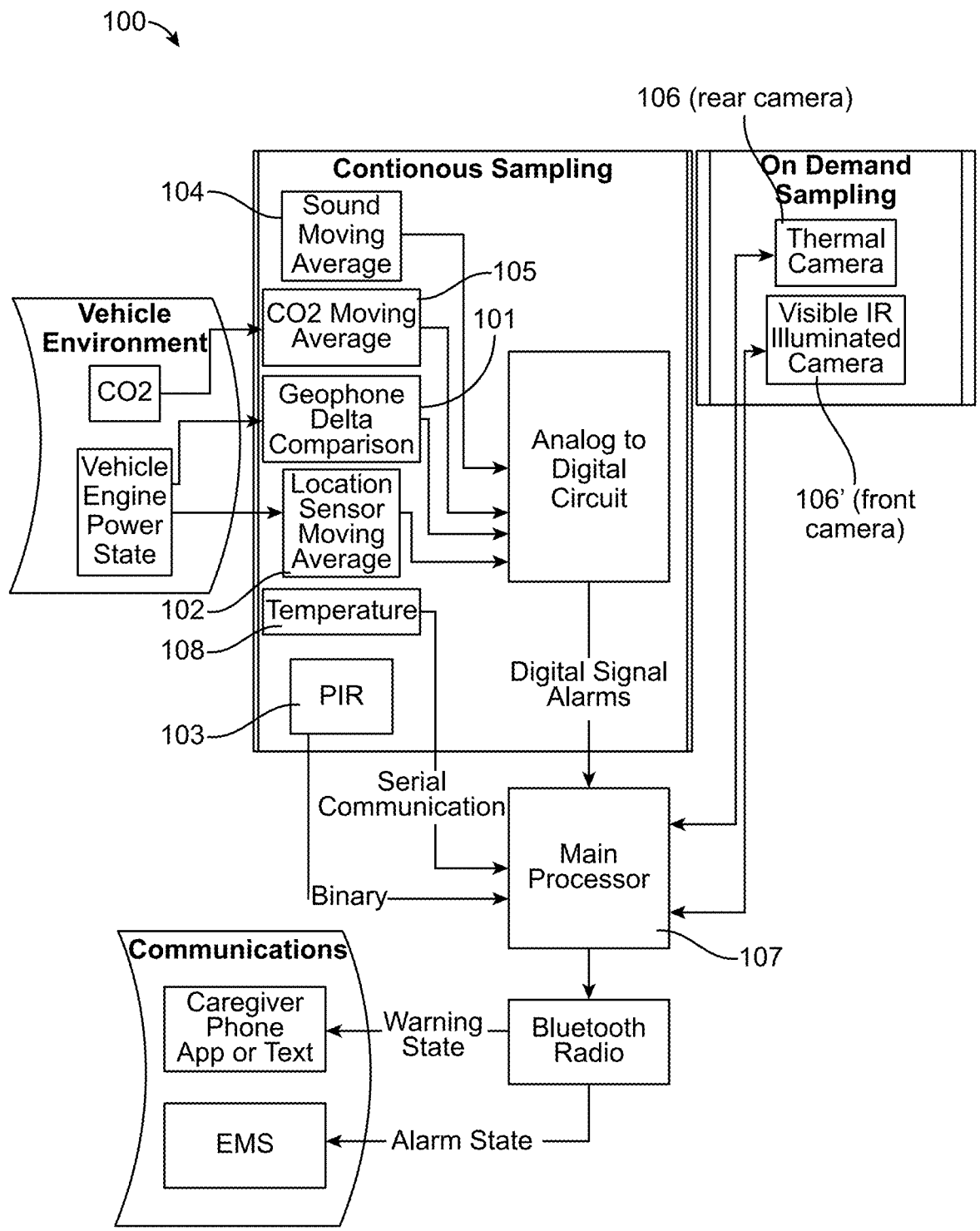

System 100 may also include one or more of a passive infrared (PIR) motion sensor 103 or sound sensor 104, or one or more cameras including thermal imaging cameras 106 to provide their respective data outputs, which may be analyzed to detect the presence or absence of a person inside the vehicle. Example cameras may comprise one or more of a front camera 106' which may be mounted to the windshield, the rearview mirror, the center console, or to the dashboard of a vehicle, or a rear camera 106 integrated into system (or module) 100 with the sensor suite and suitably mounted for example, to the ceiling of the car, or to a grab handle above the rear seat of a car. Front camera 106' may be configured to be operable with its own control module. Alternately, the two cameras 106 and 106' may bidirectionally communicate with main processor 107. For example, each camera (both front and rear) may have a power source and data transmission capabilities. Both cameras may be configured to transmit data to main processor 107 that analyzes the data and implements an example occupant detection method and related algorithm. Main processor 107 disposed in a suitable module or packaging may be mounted in the glove compartment or central console of the vehicle, or in any other suitable location inside the vehicle. As an option, the other example sensors in system 100 may also be configured to be in bidirectional communication with main processor 107 that receives data from the one or more cameras and sensors and using intelligent algorithms, may be configured to analyze data and provide safety information related to a vehicle. Example main processor 107 may comprise the Jetson Nano platform (NVIDIA). The Jetson Nano platform may be configured to run multiple neural networks in parallel in a platform that consumes about 5 W. Central computing module or main processor 107 may be configured to collect data from the imaging and physical/chemical sensors, processes the data, input the data streams into a detection/alarm algorithm, and outputs processed data and an alarm state. If unsafe or dangerous conditions are detected, main processor 107 may be configured to warn or notify occupants or external parties and trigger responses commensurate with the severity of the situation. Example detection system 100 may provide unambiguous physical/chemical information related to the presence of unattended children or pets left in a vehicle. Sensors 101-105 and 108 may be configured to sample date continuously but not necessarily continuously monitored by main processor 107. $CO_2$ values (and the output of other sensors) may be queried only if the temperature is measured to be hot or cold; that is, if the temperature is above or below a predetermined threshold. As shown in FIG. 1, cameras 106 and 106' are turned on/off as needed and on demand by main processor 107 to conserve power.

The front camera 106' for detecting drowsy and/or distracted driving may be configured to identify facial features such as eye landmarks in a range of light exposures (for e.g., day or night exposures, or other exposures) and capture both the front cabin driver and passenger in the field of view. Front camera 106' may be mounted to the windshield of the car or to the rear-view mirror. The rear camera 106 may be configured to detect the presence of an unattended person in the rear cabin. Specifications such as data rates, field of view, contrast, and resolution may be predetermined for each camera mounting position. Cameras 106 and 106' may have different fields of view and wavelengths. A child may be occluded if a single camera was aimed at both the driver (for detecting drowsy and/or distracted driving) and a child in the rear seat. A single camera may also not detect a child because a child may sit or crawl on the floor of the vehicle. Also, the imaging modality of each camera is different; that is, while thermal imaging cameras 106 may be used for detecting a human being or child or pet, they do not have the resolution (at a reasonable price point) to detect detailed facial features of a driver. Further, data collection and data analysis time for thermal cameras is less intensive than an infrared (IR) illuminated camera. Data processing times of images (video) for visible IR illuminated front camera 106' may be about 5 to 10 times longer than that required for processing thermal images output from camera 106. Cameras 106 and 106' may comprise two IR-illuminated cameras, but this may not be desirable as monitoring children with the IR-illuminated cameras would provide personally identifiable information, whereas a thermal camera preserves anonymity.

Accordingly, camera 106' may include a visible IR-illuminated camera to identify essential facial features of a driver or passenger in the front cabin at night, which may not be possible using visible-light and thermal imaging cameras. In a dimly lit environment, for example, when driving at night, a visible imager/camera may lack the contrast needed to detect any image, and the thermal imager/camera may only be able to roughly identify a body, and not the detailed facial features required for identifying drowsy and distracted driving. If the face and eye landmarks are clear to the human eye, they would be considered to be learnable features for an AI/ML machine learning engine. If an image taken using an IR-illuminated camera aimed at the driver in a bright environment lacks sufficient contrast to clearly detect how much of the eye is visible over time, the front camera module may also incorporate a visible-light imager. To detect an unattended occupant/person in the rear of a parked vehicle, camera 106 may comprise a thermal imager/camera because detecting an image of the passenger would be sufficient.

Example occupant motion sensor 103 may include pyroelectric ("passive") infrared (PIR) sensors (e.g., Model HC-SR501 PIR sensor), which may be disposed in multiple locations in example system 100 or system 200 with many view angles of the rear compartment or cabin of the vehicle. These multiple views greatly enhance the possibility of detecting occupant motion that is not in the line-of-sight of the rear thermal imaging camera 106. Furthermore, the PIR sensor may be characterized by low data rates compared to optical cameras. The response from a PIR sensor is either 0 (no motion detected) or 1 (motion detected). Example PIR motion sensor 103 may also include the digital PIR (motion) sensor for Arduino (DFRobot Gravity), which may be configured to detect infrared signals from human body and triggers with movement. PIR sensor 103 may be characterized by low power consumption and designed to run on the Arduino open-source prototyping electronics platform. Example sound sensor 104 in system 100 may include simple microphone systems configured to query the sound level in the car and may be configured to easily interface with a microcontroller. Example sound sensors 104 may include an Electret microphone amplifier (e.g., Model MAX4466), a SparkFun sound detector (e.g., SEN-12642) or similar sound sensors. The sounds inside a stopped or parked vehicle, such as the sound of a baby crying or a dog barking, may be incorporated into the decision algorithm related to example system 100. Sound sensor 104 may be configured to provide audio output, binary indication (0 or 1) of the presence of sound, and an analog representation of the amplitude of sound. Alarms may be communicated via text messages or phone calls to one or more responsible or designated parties related to the vehicle, for example, the registered owner of the vehicle, their family members, or to emergency responders or to the local police.

Figure 2A:
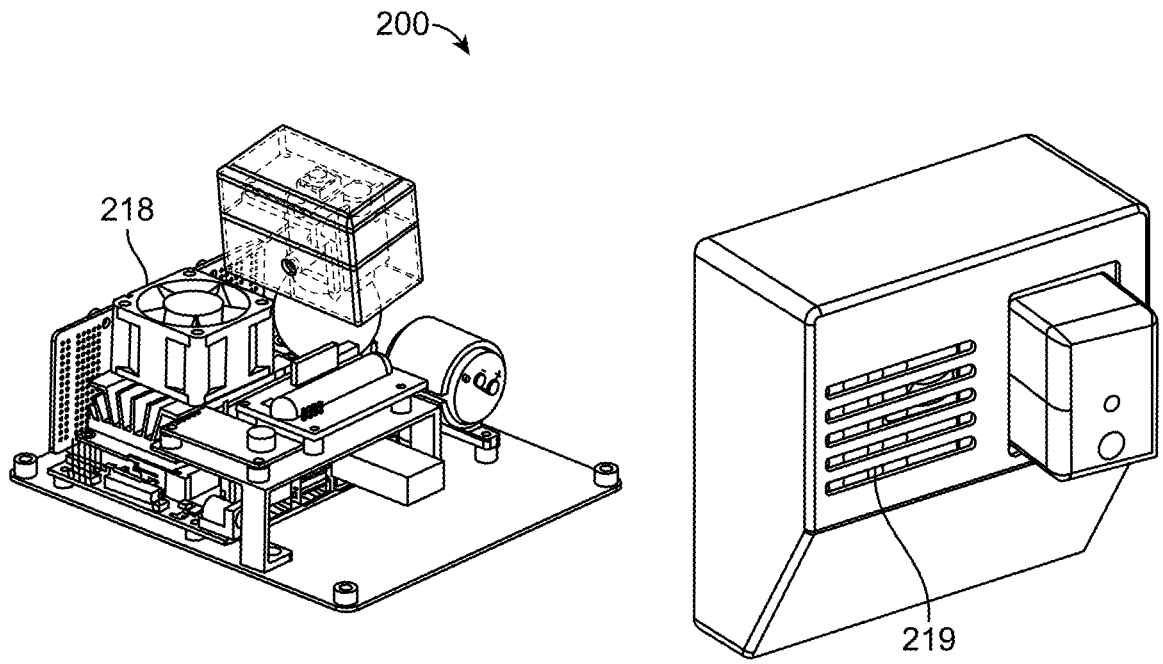
Figure 2B:
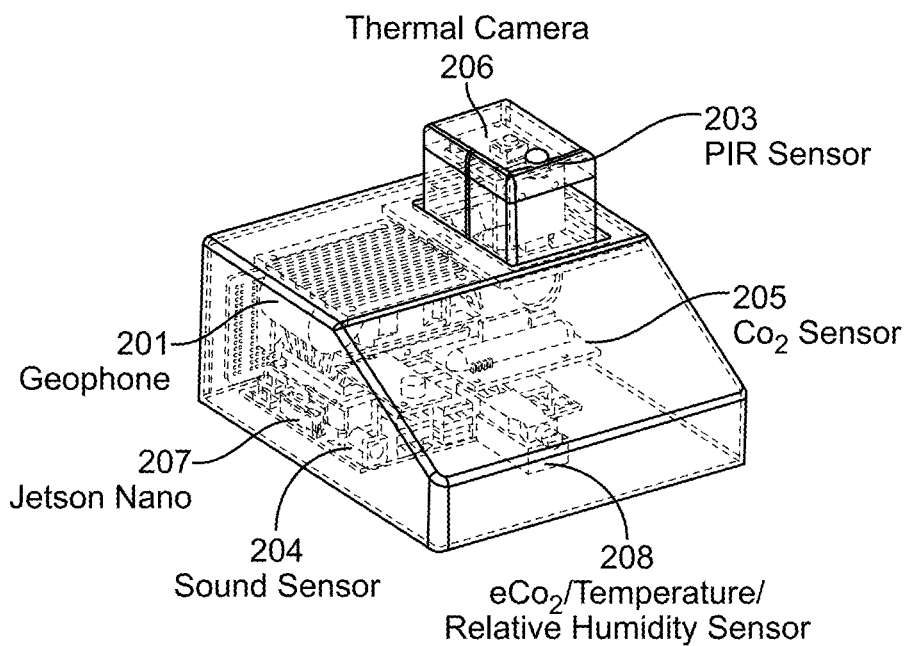

In some implementations, the plurality of sensors or sensor suite as described above may be integrated into a single package or housing 200. System 200 (FIG. 2A-B) may be powered by a portable battery. An example battery may comprise a secondary battery that may be recharged using power drawn from the vehicle while the vehicle is in motion. For example, the battery may be charged with power drawn from the car's 12 V cigarette lighter connection with cables routed through the car's overhead lining. System 200 may be configured to provide appropriate air circulation by drawing air using fan 218 through openings 219 in the housing cover to avoid any overheating of the sensors. In example system 200, an Arduino microcontroller may interface with some or all of the sensors and communicate using the I2C protocol with the primary computing system (main processor 107) based on the NVIDIA Jetson Nano platform. The Arduino microcontroller may be configured to communicate with $CO_2$ sensor 205 (e.g., DFRobot, Gravity PWM infrared $CO_2$ sensor), a microLED display 216 (FIG. 7), geophone sensor (e.g., SM-24, Sensor Nederland, b.v.) or digital compass/magnetometer 201, and integrated temperature/humidity sensor/$eCO_2$ sensor 208 and pass data to the main processor 207 such as a NVIDIA Jetson Nano platform via the I2C bus. A standalone metal oxide $eCO_2$ sensor (e.g., Adafruit CCS811) may also be connected to the I2C bus.

PIR motion sensor 203 and sound sensor 204 may be connected directly to the Jetson Nano platform through a pHAT carrier bus. Thermal imaging camera 206 in system 200 may be connected main processor 207 using the built-in USB bus.

Figure 3:
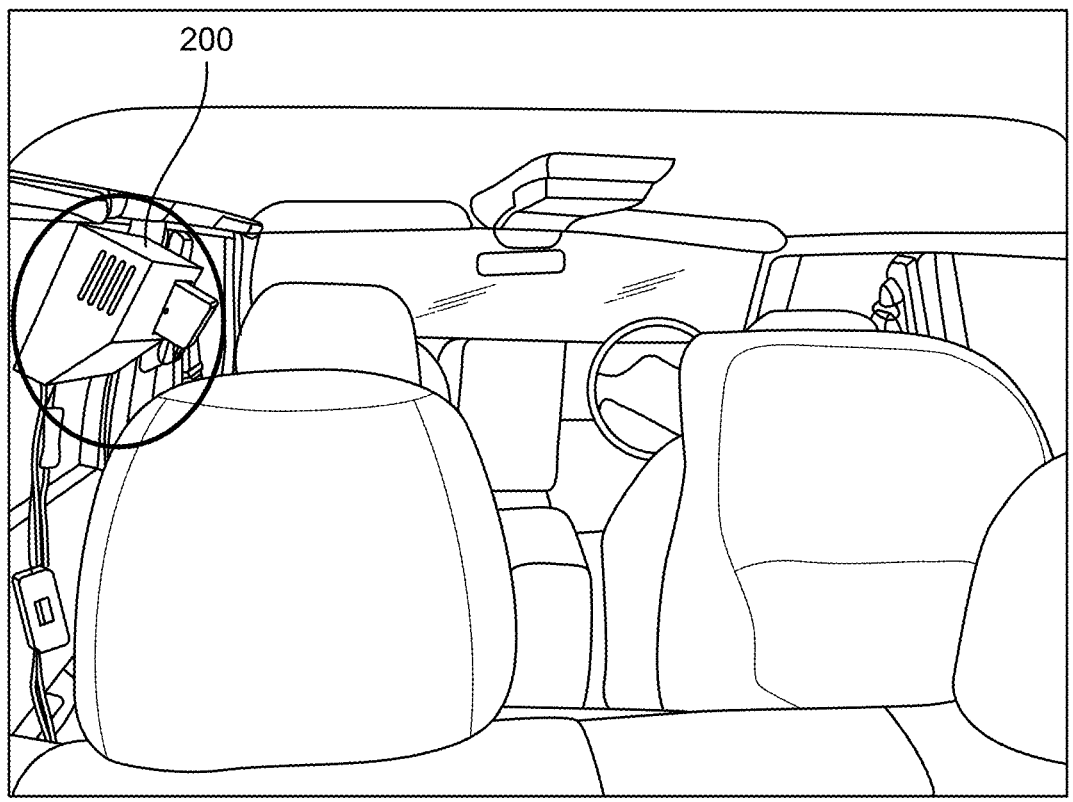
FIG. 3 shows a photograph showing an example detection system 200 mounted inside a vehicle, according to some implementations.

Thermal camera 206 (e.g., FLIR Lepton, 95° field of view) may comprise a longwave infrared camera comprising an uncooled VOx microbolometer detector. Thermal cameras with 120-degree, 150-degree, or 170-degree field-of-view may also be used. Thermal camera 206 and PIR sensor 203 may be mounted on an adjustable swivel mount. The thermal spectral range of an example camera 206 may comprise longwave infrared ranging from about 8 μm to about 14 μm and may be configured to capture calibrated and noncontact temperature data in every pixel of each image. System 200 may be configured as a low-cost detection system that may be easily manufactured for an OEM or aftermarket component in vehicles. The plurality of sensors as described above in example system 100 or 200 may cost less than about $300 in low volumes. Example system 200 may be mounted in any suitable location inside a vehicle. In some implementations, detection system 200 may be configured to be removably mounted (FIG. 3) to a grab handle above the rear seat of a vehicle and may be positioned to capture images of occupants in the one or more rear seats of a vehicle. In example system 200, an appropriate data collection rate for each sensor may be determined by taking into account the capabilities of each sensor hardware, data processing hardware, and the requirements of the intelligent detection algorithm (e.g., method 400). Data rates may likely be different for different sensors. Example data rate of 0.2 hertz (Hz) for the $CO_2$ sensor and a data rate of 10 Hz for all other sensors may be used. Data rates may be optimized to realize the low false alarm rates targeted for detecting unattended occupants in a vehicle. System 200 may be set up to log sensor data as a function of time into memory. System 200 may be configured to communicate with a remote server to capture and process data measured by one or more of the geophone vibration sensor, the temperature sensor, or the $CO_2$ sensor or other sensors and camera images. An Arduino or Raspberry Pi computing/controller platform may be used to provide connectivity to the sensors along with the underlying Opensource code for interfacing to the sensors.

Figure 4A:
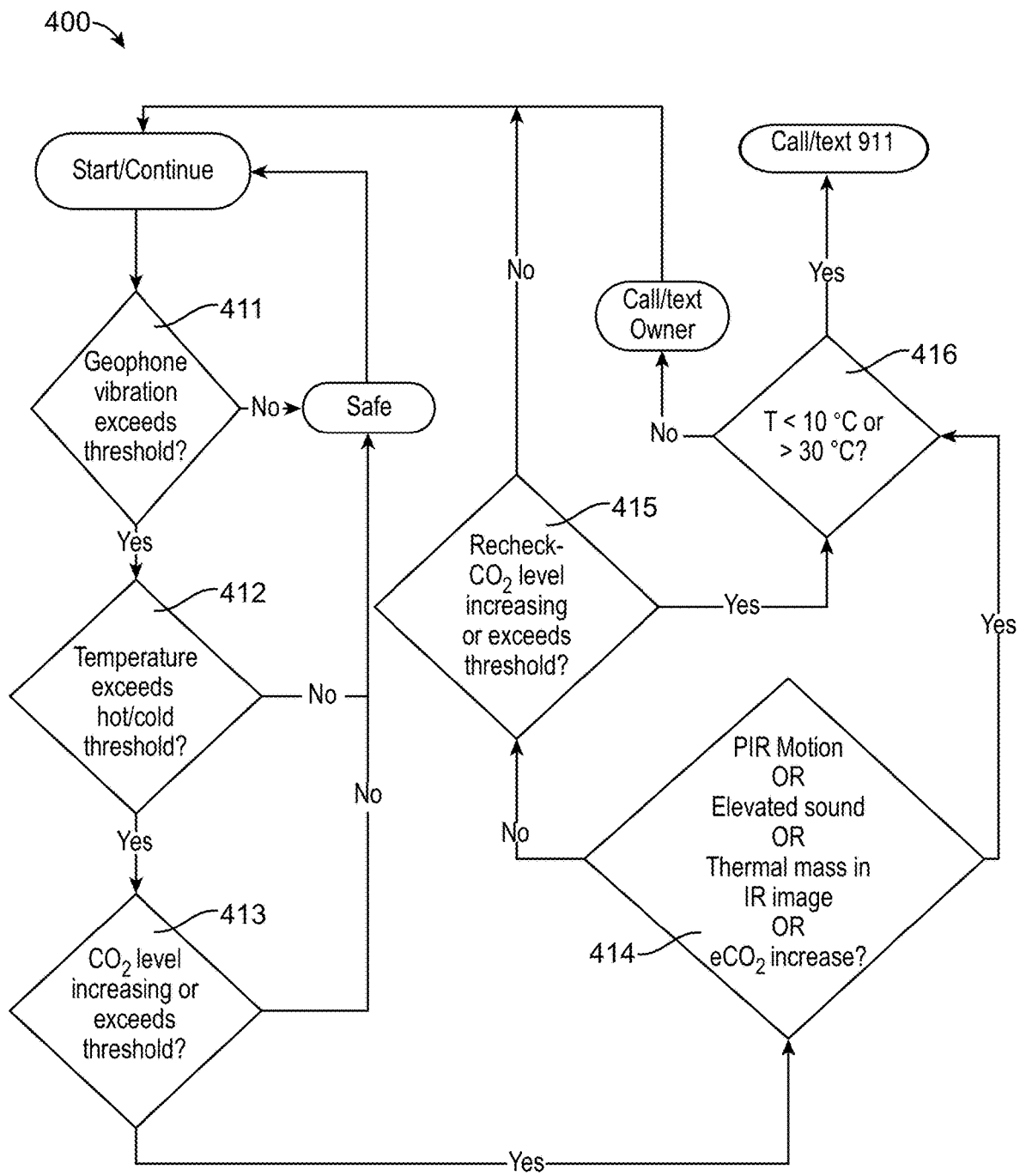
FIG. 4A shows a schematic diagram of an example method for detecting an unattended person in a vehicle, according to some implementations.

Disclosed is an example method 400 (FIG. 4A) for detecting an unattended occupant in a stationary vehicle. The example method may be configured to answer three questions, namely, (a) is the car in motion? (b) is the car hot or cold? and (c) is there a person in the car? These questions may be addressed in sequence in a feedback loop; that is, whenever the answer to any of these three questions is a safe state, the loop returns to the start position. Step 411 may use example geophone sensor 201 to detect vibration from a car equipped with example system 200. Measured vibration above a predetermined threshold may indicate that the vehicle is not stationary, and the inquiry related to an unattended person or child stops. Alternately, as geophone voltage signals are collected as moving average. A difference in voltage between the exponential moving average of about four data points (current reading) and that of a previous reading ($\Delta V = V_{ave,t} - V_{ave,t-1}$) that less than or equal to about 0.1 V may indicate that the vehicle is stationary. If $\Delta V$ is greater than about 0.1V, this suggest that the vehicle is moving and the inquiry into an unattended occupant can stop. If the geophone sensor signal indicates that the vehicle is stationary, then the inquiry may proceed to step 412 to examine whether the temperature inside a car is above or below a predetermined safe threshold. For example, a predetermined safe threshold may be below 10° C. or above 30° C. For example, the temperature inside a stationary car (cabin temperature) with at least one window partially opened or closed or with the air conditioning system running may not fall below or exceed a low temperature/high temperature threshold. The rate of increase in temperature may also be monitored, for example using example sensor integrated sensor 208. If the temperature inside the vehicle exceeds a predetermined threshold, the $CO_2$ levels in the car may be monitored in step 413 to examine if the $CO_2$ level is increasing or exceeds a predetermined threshold. That is, while the $CO_2$ sensor is continuously measuring $CO_2$ levels, data is not continuously monitored by main processor 107. Only if the temperature is measured to be above or below hot or cold temperature thresholds respectively, will the $CO_2$ levels be queried by main processor 107. $CO_2$ related data collection is not data intensive or power intensive. In contrast, the cameras are characterized by greater power draw and are turned on/off by processor 107 as needed.

Alternately, step 413 may precede step 412. That is, if the geophone sensor signal indicates that the vehicle is stationary, then the inquiry may proceed to step 413 to examine if the $CO_2$ level is increasing or exceeds a predetermined threshold. If the $CO_2$ level is increasing, then cabin temperature may be monitored to examine whether the temperature inside a car is above or below a predetermined safe threshold. For example, a predetermined safe threshold may be below 10° C. or above 30° C. The rate of increase in temperature may also be monitored, for example using example sensor integrated sensor 208.

A predetermined threshold for $CO_2$ levels may be between about 300 ppm and about 400 ppm, which is the $CO_2$ concentration range in ambient air. An example $CO_2$ sensor may comprise an infrared $CO_2$ sensor 205. Since increasing $CO_2$ levels are indicative of exhaled breath accumulation in a closed space or closed vehicle, more than one $CO_2$ sensor may be used. As previously noted, integrated sensor 208 may be configured to output $eCO_2$ levels. If the $CO_2$ level is increasing or exceeds a predetermined threshold in step 413, one or more of the outputs of the PIR motion sensor 203, sound sensor 204, or thermal camera 206 may be examined in step 414 to confirm the presence or absence of an unattended occupant/person in a stationary vehicle. The $eCO_2$ output from integrated sensor 208 may also be examined. If the output in step 414 does not suggest the presence of an unattended person, the output of $CO_2$ sensor 205 may once again be examined in step 415. If the output of steps 415 suggests that an unattended occupant is present in the vehicle, temperature inside the vehicle may be checked in step 416, to examine, for example, if a car door has been opened which would indicate that the passenger or person in the car is no longer unattended. The example method may be configured to contact one or more of the owner of the vehicle, designated contact persons, law enforcement or emergency medical services. For example, if the temperature monitored in step 416 is in a safe range, that is, not <10° C. or not greater than 30° C., a warning message may be communicated to the car owner. If the temperature monitored is not in the safe range, then law enforcement or emergency medical services may be contacted. Energizing sensors (turning sensors ON/OFF) using a step-wise predetermined protocol as described above may help to conserve power consumption by the various sensors in system 200 and extend battery life. As previously described, since detection systems and methods could raise significant negative consequences in the event of a false detection or alarm, low false alarm rates are targeted by employing a detection system that is configured to provide multiple independent data streams from various sensors for analysis.

Example decision states (thresholds) that may feed into method 400 may include:
(a) Motion State
　0, (vehicle is stationary with engine on or off) if the difference ($\Delta V$) between the exponential moving average of a predetermined number of data points of the geophone sensor voltage signal at time ($t_n$) and at a previous time ($t_{n-1}$) is less than or equal to about 0.1 V. The number of data points may be between about 2 and 10.
　1, (vehicle is moving) if $\Delta V$ is greater than about 0.1V.
(b) Temperature State
　0, if the temperature is less than about 10° ° C. or greater than about 30° ° C.;
　1, otherwise.
(c) Signs of Life State
　0, if the exponential moving average of $CO_2$ concentration rate of change is less than about 0.2 ppm/s;
　1, otherwise ($CO_2$ steadily increasing).
(d) Alarm State
　0, if Motion State=0, or Temperature State=0, or Signs of Life State=0
　1, otherwise.

Figure 6:
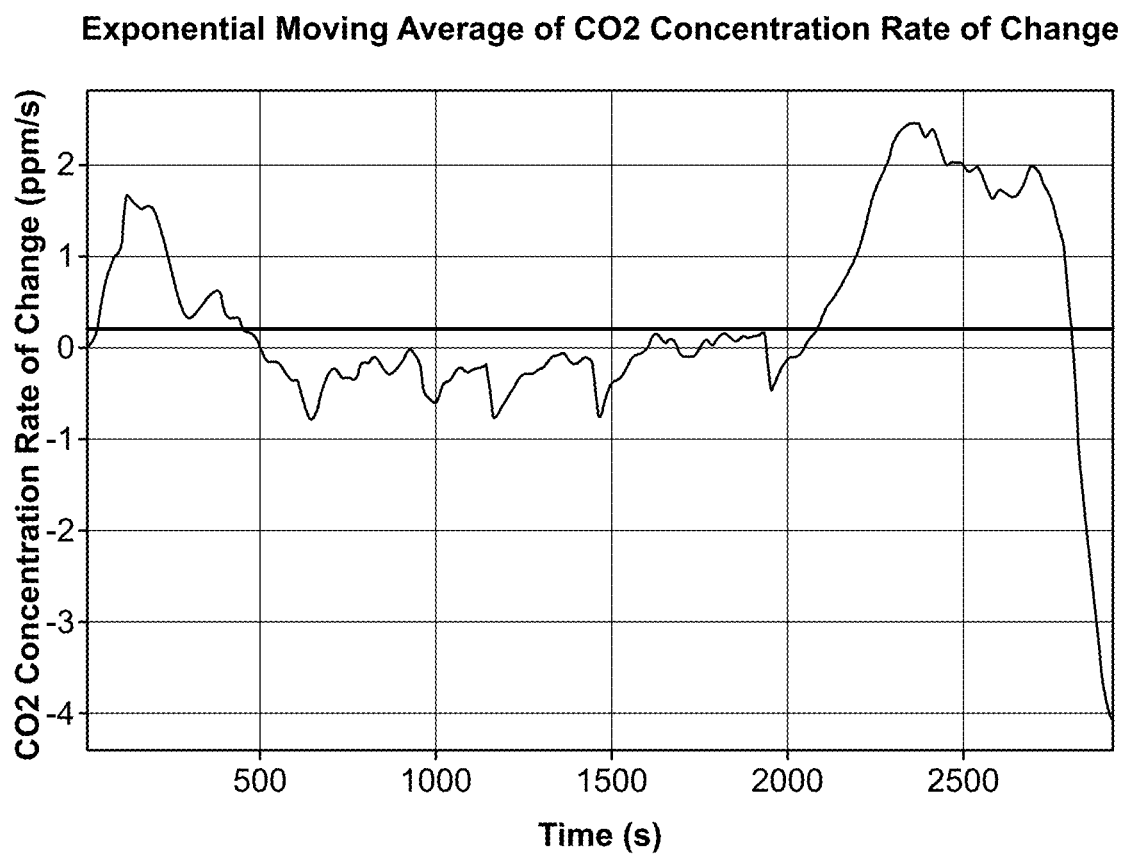
FIG. 6 show graphical representation of conditioning the signal from the $CO_2$ sensor, according to some implementations.

The signal (outputs) from the one or more sensors may need to be processed prior to being used in the decision state matrix as describe above. For example, the raw voltage signal from geophone vibration sensor 201 may be too noisy to interpret, and may require exponential moving average (as described above) to smooth or condition the output data. A $\Delta V$ value that exceeds 0.1 volts may indicate that the car is in motion or being driven. Since a car in motion, eliminates the possibility of an unattended child, a $\Delta V$ value that exceeds 0.1 V eliminates the possibility of the presence of an unattended occupant/child in the car. If car is parked, with engine on, $\Delta V$ may be between 0.01 and 0.025 V. Similarly, the output of the $CO_2$ sensor 205 may also be too noisy. As shown in FIG. 6, an exponential moving average of $CO_2$ concentration (sensor output signal) may be used to smooth or condition the signal. A rate of change of the conditioned signal may then be computed. An exponential moving average of $CO_2$ concentration rate of change which exceeds 0.2 ppm/s (horizontal line) may be indicative of an unattended person in a parked car/vehicle.

In order to identify a threshold for each sensor to trigger an alarm, an examination of sensor data collected under normal conditions would be required to acquire background or baseline data. For example, data collected when a car is in motion, when a car is neither hot nor cold, and when no one is trapped in the car would be required to acquire baseline data. Deviations from baseline data will indicate a possible trigger for an alarm, and multiple sensors indicating deviations from their respective backgrounds will strengthen the likelihood of a real trigger. FIG. 7 summarizes representative $CO_2$ levels in a large sports utility vehicle (SUV, 5000 L internal volume). It is well-established that the tidal human breath volume is about 7 mL/kg of body weight. The number of breaths (exhale/inhale) per minute may vary from about 15 breaths/min in adults to about 45 breaths/min in children. Using this information, the breath volume output per minute may be calculated. Since the $CO_2$ level in human (and other mammals) exhaled breath is approximately 4%, the volume of $CO_2$ exhaled per minute allows may be calculated. The $CO_2$ concentration expected from an adult breathing in a parked and closed SUV after one hour may be calculated. For example, the $CO_2$ level inside the SUV may approach 1800 ppm for a person who weighs about 45 kg. The last column in FIG. 7 (right most column) provides the expected $CO_2$ concentration in a small car with about half the internal volume. Low-cost $CO_2$ sensors may be characterized by a noise-equivalent sensitivity of less than about 50 ppm. For a child weighing about 5 kg in a large SUV, the expected rise in $CO_2$ may be about 0.12 ppm per second. Even under these conditions, the $CO_2$ sensor could determine the presence of a child in a hot car within a period of between about 5 min. and 10 min. A similar analysis may be used to establish the alarm triggers for the other sensors. Once an alarm state is determined by the example algorithm (or example method 400), an appropriate response may be executed, ranging from alerting the driver with an audible message, notifying the authorities, or initiating cooling measures in the car (FIG. 5). Bluetooth and Wi-Fi communication protocols may be used. A number of modules exist to enable Bluetooth and/or Wi-Fi capabilities on the Jetson Nano, including USB plug-ins. In parallel, a LED light may also be activated to indicate that an alarm state has been identified.

Compiling varied and sizeable datasets that resemble real driving scenarios is essential for training neural networks to generalize to a broad range of situations. It may be time and resource-intensive to collect (and label) a significant amount of data and images. Alternately, when faced with limited training data, a dataset may be developed using data augmentation, which includes a number of techniques to increase the amount of data by applying random but realistic transformations to an existing data set. Basic techniques include flipping, rotating, cropping, zooming in/out, and changing the brightness or contrast of images. In addition to collecting images in a car in real driving scenarios, laboratory-simulated images may be developed using data augmentation techniques. A neural network may be trained identify a drowsy driver by monitoring the driver's gaze; that is by monitoring the driver's face, then the driver's eyes, and then to detect how much of the eyes are visible over time. Similarly, learning a driver's head position over time may be useful because a drowsy driver's head tends to dip. A similar approach may be used to train a dataset to identify distracted driving. For implementing models on hardware, the NVIDIA Jetson Nano computer platform (main processor 207) may be used taking into account factors such as on cost, size, processing power, and software availability. Machine learning frameworks that include, but are not limited to, TensorFlow or PyTorch may be used. Embedded hardware may be deployed using PyTorch as it has seen strong adoption in the automotive industry.

Figure 4B:
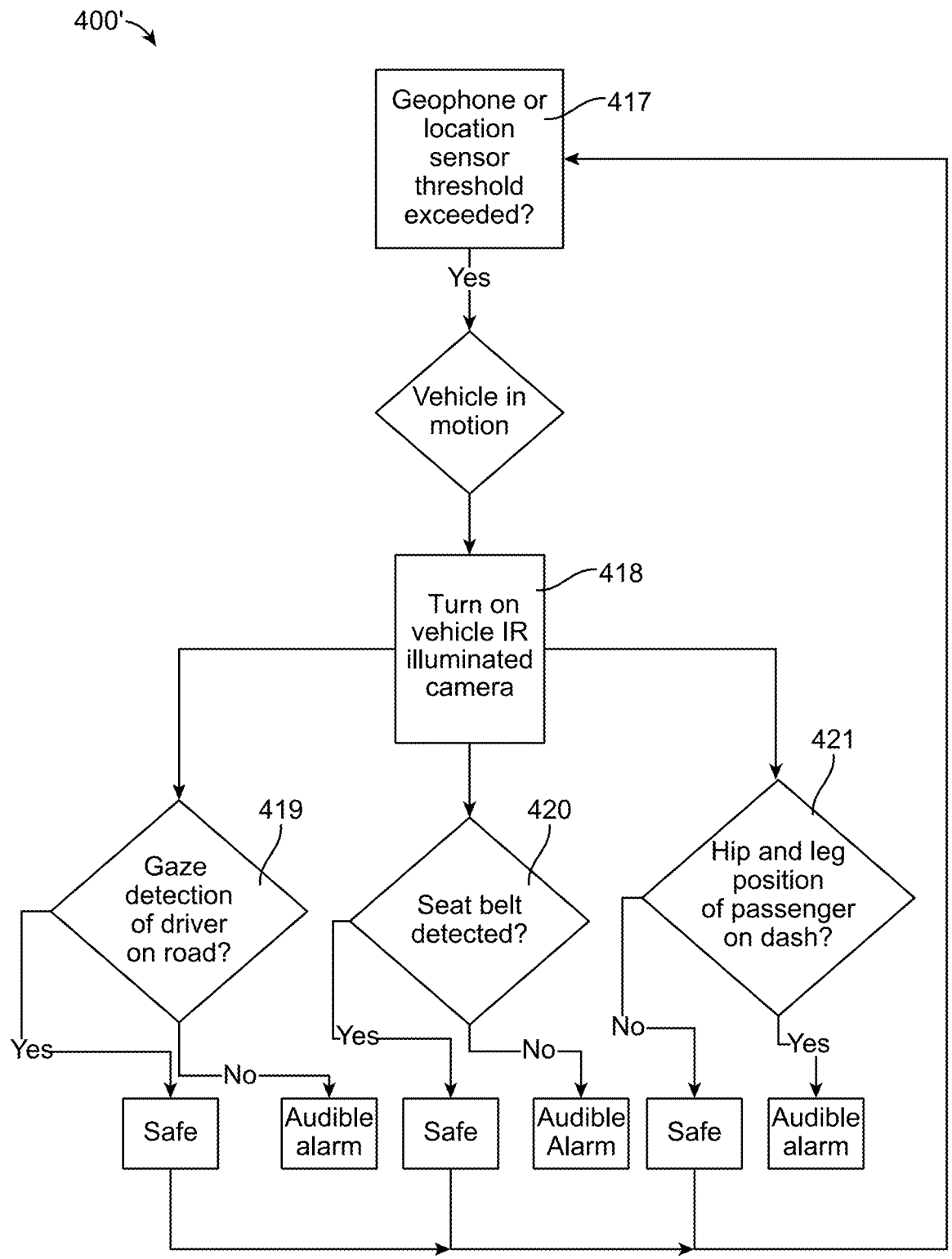
FIG. 4B shows a schematic diagram of an example method for detecting drowsy or distracted driving, according to some implementations.

The data streams from the disclosed in-vehicle safety and unattended occupant detection systems 100 or 200 or 700 may feed one or more detection algorithms for vehicle occupant safety based on method 400 or a modified method 400' (FIG. 4B) that is adapted to detect distracted and/or drowsy drivers. As previously described, a $\Delta V$ value related to a geophone sensor signal (step 417) that exceeds a threshold of 0.1 V may indicate that the car is in motion or being driven. For the sake of clarity, $\Delta V$ represents the difference in voltage of the geophone sensor signal between the exponential moving average of about four data points (current reading) and that of a previous reading ($\Delta V = V_{ave, t} - V_{ave, t-1}$). A suitable threshold may be established for other location sensors also. After confirming that the vehicle is in motion, main processor 107 or an equivalent processor may turn on the visible IR illuminated front camera 106' to monitor the gaze of the driver in step 419, proper seat belt use in step 420 and to monitor whether the passenger sitting next to the drive is sitting in an unsafe position with legs on the dashboard in step 421. Unsafe conditions detected in steps 419-421 may trigger an audible alarm. Safe conditions return the detection method to step 417. The driver and passenger may be monitored continuously, for example, during night driving, or at pre-determined intervals to optimize monitoring and data processing capabilities of processor 107 or an equivalent processor.

The output from the algorithm that underpins the example systems 100 or 200 or 800 may be used to trigger tailored communication and responses related to dangerous driving conditions or to unattended occupants within a parked vehicle. The type of response, and urgency of the response may follow a predetermined hierarchy. For example, detection of a drowsy driver in step 419 (FIG. 4B) may simply trigger an audible alarm that alerts the driver to take corrective action. An example response matrix to various in-vehicle safety compromising conditions is shown in FIG. 5. Additional components may be integrated into the example detection systems disclosed herein. For example, main processor 207 does not have speakers, Bluetooth, or Wi-Fi communication capabilities built in, but USB plug-ins may be installed to provide these functionalities. The determination of an alarm state may be based on data from the front camera(s), rear camera(s) at appropriate frame rates, and sensor suite and output from the AI/ML deep learning models. The main processor 207 (e.g., Jetson Nano) may be configured to process the data from each of these three data sources and feed it to a detection algorithm.

In order to train a neural network to recognize drowsy/distracted driving, the model must be fed labeled images, where some exhibit drowsy/distracted driving behavior and others do not. To simulate drowsy/distracted driving without violating any laws in the U.S., a right-hand drive car may be used while the passenger/actor sitting at the left-hand side of the front cabin equipped with a dummy (inoperable) steering wheel and pedals may act as a drowsy/distracted person. Rather than driving drowsily, the participant may be instructed to pretend to drive while directing most of their attention on something other than the road, such as a mobile phone. Participants/actors may also be encouraged to feel and act drowsy, since they will not truly be operating a vehicle. The data collection may only take a few minutes. For example, the image frame from the front camera 106' may be saved every 0.5 seconds over the course of a five-minute period while driving the vehicle with the drowsy/distracted actor/participant. A test period of five minutes will yield 600 saved images from one test. The simulated drowsy/distracted test may be repeated with multiple drivers 40-50 times to yield 24,000 to 30,000 saved images. In addition to the images which are representative of drowsy/distracted driving behavior, images representative of non-drowsy/non-distracted driving behavior may also be collected. This data collection may yield in total about 50,000 to 60,000 images for labeling and classification. As previously described, the number of images may be increased further by data augmentation. A relatively new and promising way to generate more training images is to use a generative adversarial network (GAN), which are neural networks that provide a domain-specific approach for generating synthetic data. GAN may create new, artificial but plausible examples from the input data on which the model is trained.

Images for examining un-safe seatbelt use in the U.S. may be collected using an ordinary left-hand drive parked car. During image/data collection, the camera frame may be saved every 0.5 seconds for five minutes. First, each participant may be instructed to pretend to drive while wearing the seatbelt, followed-by pretending to drive with the seatbelt off, and finally pretending to drive with the seatbelt improperly buckled. Data may be automatically labelled based on the test condition established for the given five-minute period. To examine unsafe occupant positions in the front cabin of a car, images may be collected in a left-hand drive parked car with the same protocol used for improper seat-belt use. However, the participant will be positioned in the passenger seat. An example unsafe position may include the passenger sitting with legs on the dashboard. Each participant will be instructed to sit in the normal safe position with seat-belt on and in various unsafe positions. About 50,000 images may be collected for each unsafe scenario, prior to any data augmentation.

It is also important to distinguish between models that will apply to images and models that will apply to sequences of images. Classification of seatbelt use, occupant unsafe positions, and unattended occupant presence may use models that apply to images. Classification of drowsy/distracted driving may use models that rely on a sequence of images. For the models that apply to images, the approach may include picking a model class, for example, a residual neural network (ResNet), and an initial architecture, for example, ResNet-18, and measuring accuracy between actual images and model predictions after training using a train/dev/test split to set-up the training, development (dev) and test sets. The dev instances may be used to tune hyperparameters like learning rates and batch size for calculating train/test accuracy. Two important questions to address are (a) whether the model fits the training data and (b) whether the model can be generalized to process and predict new data. For example, Google AI has developed lightweight models known as the EfficientNets family of models that offer better accuracy and efficiency than ResNet. Different models may be examined to optimize speed, accuracy, and efficiency and may include EfficientNets models such as MobileNet and SqueezeNet.

After training, the accuracy related to the training data may be measured. If the model cannot be trained to high accuracy (for example, at least 90% accuracy) on the training data, then the model selection will be revisited in favor of a larger model with more parameters. If training accuracy is acceptable, test accuracy may be evaluated. If the test accuracy is low, more data may be needed or the model may be overfitting, in which case a smaller model may be needed or methods to avoid overfitting may be used.

A similar approach may be used for models that are fed sequences of images. Models that need memory units (e.g., LSTM cells) may be used for recognizing drowsy and distracted driving characterized by the driver's eyes being closed for a relatively long time as opposed to a short natural eye blink. For these residual neural networks, the approach may examine making the model larger or smaller, adding more data based on the relative training/testing accuracies until the testing and training accuracies are similar.

After tuning hyperparameters, the model training process may involve searching over the space of hyperparameters for settings that give good performance or high accuracy. A number of methods may be used including Hyperopt, a Python library for hyperparameter optimization and determining a reasonable set of hyperparameters using the validation set. In addition to using accuracy to assess model performance, integrated gradients may be used to identify the important features that contribute to model predictive capabilities. For example, the seatbelt model must know to look at the seatbelt in the image to predict proper/improper seat-belt use. Using autoencoders for anomaly detection, for example, to distinguish between normal driving and drowsy/distracted driving, or between the presence and absence of an unattended occupant is within the scope of the example systems and methods disclosed herein.

In some other implementations, an in-vehicle unattended person detection system 800 (FIGS. 8-10) may include a transponder unit 801 and receiver unit 802. Transponder unit 801 may house and may be configured to collect data from $CO_2$ sensor 205, sound sensor 204, PIR motion sensor 203, and temperature/RH/$eCO_2$ data from integrated sensor 208 (FIG. 9). Thermal camera 206 may be housed in transponder unit 801 and may be turned ON/OFF to confirm the presence of an unattended occupant in the car, for example, in accordance with the protocol disclosed under method 400. Transponder unit 801 may configured to be removably mounted to a grab handle above the rear seat of a vehicle (FIG. 8) using clamps 211 and may be positioned to capture images of occupants in the one or more rear seats of a vehicle. Transponder unit 701 may be powered using a rechargeable battery 209, for example, a 5.8 Ah, Li-ion battery. Battery 209 may be recharged from any power source including power drawn from the vehicle while the vehicle is in motion. Thermal camera 206 and PIR sensor 203 may be mounted on an adjustable swivel mount 210 in transponder unit 801. Motherboard 212 may support a suitable microcontroller, Bluetooth wireless components to communicate with the receiver unit 701 and a battery charging circuit. Example dimensions of transponder unit 701 may be about 8.5 in. (L)×5 in. (W)×4.5 in (H).

Receiver unit 802 may be configured to collect data from geophone sensor 201 (FIG. 10) and to collate data received from the transponder unit 801 and run the detection algorithm based on a predetermined detection protocol, for example, the protocol disclosed earlier as method 400. Receiver unit 802 may be configured to be removably mounted using clip 217 to the center console located between the driver seat and the front passenger seat. Receiver unit 802 may be powered using a rechargeable battery 214, for example, a 5.8 Ah, Li-ion battery. Battery 214 may be recharged from any power source including power drawn from the vehicle while the vehicle is in motion using power cord connection 213. Motherboard 215 may support a suitable microcontroller, Bluetooth wireless components to communicate with the transponder unit 702 and a battery charging circuit. An LCD display screen 216 (FIG. 10) may provide battery charge status and also status of any alarms.

Some other example implementations of an in-vehicle detection/monitoring system to detect distracted and/or drowsy drivers may include a front camera which may be mounted on the windshield of a vehicle. An example front camera module may comprise one or more of visible, IR-illuminated, or thermal imagers. An IR-illuminated camera may outperform the thermal camera because of its ability to capture detailed features such as eye landmarks, which may be used to identify drowsy and distracted driving. Since an IR-illuminated camera may be unable to perform well in broad daylight, the front camera module may include a visible camera as well. Since the only computer vision task of the rear camera disposed in example system 200 or in transponder unit 801 is to detect the presence of a person, a thermal camera 206 may be sufficient for imaging rear passengers when needed.

Camera resolution and field of view are two considerations for in-vehicle passenger monitoring and detection safety systems. While increasing the resolution makes images clearer, it also makes images larger, which is more computationally intense. With cameras that have very high resolution, images are often compressed during machine learning for ease of processing. On the other hand, if the resolution is too low, it can be difficult to identify features in images. Examples of thermal imaging cameras may include one or more of FLIR Lepton 2.5 and Lepton 3.5. The FLIR Lepton 2.5 thermal camera has a modest resolution of 80×60 pixels. The Lepton 3.5 has a resolution of 160×120 pixels and may produce crisper images. The array size of the Lepton 3.5 camera is closer to the input dimensions (224× 224) of example neural networks which may be used for image processing and machine learning purposes, as it leaves less room for distortion due to resizing interpolation methods. The FLIR Lepton 3.5 camera array format may be large enough to be able to discern features but not so large that the images are especially taxing computationally, which may make it a better choice than the Lepton 2.5 for in-vehicle passenger monitoring and detection purposes. The Lepton cameras may be used with a UVC FLIR Lepton smart I/O board with a low frame rate (9 Hz) FLIR Lepton thermal imaging module.

Regarding the field of view, capturing both the driver and passenger images in the front cabin with the same camera may be preferable for several reasons. For example, captured images from a single camera may be repurposed for different tasks such as detecting distracted and/or drowsy drivers, texting while driving, improper seat-belt use, legs on dashboard or unattended in-vehicle passengers, which reduces data collection and storage needs. It is also easier and cheaper to package one camera instead of multiple cameras in the example detection and monitoring system. Finally, it is computationally easier to render fewer images at any given time. A camera's technical specification and placement within the vehicle may dictate whether a single camera may be used in the example monitoring and detection systems. Neither the 57° Lepton 3.5 nor a 95° Lepton camera was found to encompass the entire front cabin when mounted on the rearview mirror. A high-field-of-view camera (95°) mounted on the windshield may be used to capture both the driver and passenger within the front cabin of the vehicle.

EXAMPLE

Example 1. Response from a Plurality of Sensors in Example In-Vehicle Unattended Person Detection System 200

Example in-vehicle unattended person detection system 200 was mounted in a car as shown in FIG. 2 and data from the various sensors was collected as a function of time over a period of about 50 min. Various events during the test period are summarized in Table 1.

TABLE 1

Summary of events during performance of example system 200 installed in a car.

| Event/Epoch | Approximate time (s) | Description |
| --- | --- | --- |
| 1 | 250 | Engine on, car stationary |
| 2 | 750 | One adult enters car, turns on heat and drives |

TABLE 1-continued

Summary of events during performance of example system 200 installed in a car.

| Event/Epoch | Approximate time (s) | Description |
| --- | --- | --- |
| 3 | 2000 | Park car, turn off heat |
| 4 | 2100 | Turn off engine |
| 5 | 2750 | Open door |

As shown in FIG. 11, geophone sensor 201 detects the vibration of the car when the car is in motion between about 750 s and about 2000 s. Since the car heater is turned on during driving, an increase in temperature and decrease in relative humidity is seen (output integrated sensor 208). $CO_2$ levels are fairly flat during driving. When the car is parked with the driver inside and the engine is turned off (between about 2100 s and about 2750 s), $CO_2$ levels inside the car clearly increase, which is indicative of exhaled air from a person inside a parked car. The output of the $CO_2$ sensors suggests that $CO_2$ levels may be monitored using one or more of sensor 208 or sensor 205 when the car is parked, that is, when no vibration of the car (from sensor 201) is registered. During this period, the humidity level also increases inside the parked car with closed doors and windows. The output of the sensor system 200 as described above suggests that the geophone vibration sensor and $CO_2$ sensor may be viewed as primary sensors to detect an unattended person in a parked car with doors closed. The PIR sensor 203, sound sensor 204, and thermal camera 206 may be viewed as confirmatory sensors, which may be triggered after an increase in $CO_2$ levels at no car vibration is detected. Upon opening the car door, $CO_2$ and humidity levels decrease as expected.

The example systems and methods disclosed herein may be configured to communicate with a mobile application software ("app") which may installed on a car owner's mobile device. A mobile application software or "app" is a computer program configured to run on a mobile device such as a smart phone, tablet or watch. A user or car owner may then have real-time access to the one or more cameras incorporated in the example systems and methods to check the inside of the car for an unattended person, to monitor a child or elderly parent driving at night or talk to a driver or to an unattended person. Alternately, taking into account privacy/security concerns, the app may provide for one-way communication where the mobile application notifies the user of dangerous situations without explicitly stream data. An app comprises a front-end component or user interface ("UI") and is designed to provide the user with an easy-to-use and friendly interface. The front end communicates with a back-end component which facilitates data routing, security, authentication, authorization, working off-line, and service orchestration. An app may also communicate with one or more intermediate or middle components including, but not limited to, mobile app servers, message queuing, enterprise service bus ("ESB") and other service-oriented architecture ("SOA") infrastructure components. Data synchronization between the mobile device and a database or cloud and offline (without internet connection) capabilities are key to the seamless functioning of successful mobile apps. Providers of database and cloud services such as Couchbase Mobile (Couchbase), Azure Mobile Services (Microsoft), Cognito (Amazon), Firebase (Google) offer synchronization and offline capabilities with their mobile offerings. The app should preferably provide for secure data access communication with synchronized and decentralized storage, transmission and storage using features such as address authentication, data at rest, which relates to whether the app supports file system encryption and data-level encryption, data in motion and read/write access that defines what data may be accessed and changed/modified by users. Databases may be relational (SQL databases such as Oracle, mySQL) or NoSQL (e.g., MongoDB, CouchDB). Further, for decentralized data writes on mobile platforms, the same data can be simultaneously modified on multiple devices and may create a conflict between data access from multiple devices. The app should preferably incorporate a mechanism for resolving those conflicts. The conflict resolution mechanism may allow resolution automatically, on the device, in the cloud, or could be manually initiated.

Further, a car owner may request assistance through the app from a relative or the emergency responders (e.g., 911). System responses triggered upon identification of one or more safety events (FIG. 5) may be routed to the car owner and other nominated people through the app. Security features may be built into the app. For example, techniques, protocols, and tools that enable the data to be encrypted, to enable the system to verify that the device used to transmit the data is actually owned by the user, to ping a user's device (e.g., text message, push authentication and the like) to check if the user's device is ready to receive data or reports sent from the server to the user's device may be used. Alphanumeric password protection may also be used. Alternately, the app on the user's device may be capable of verifying and allowing any communication from a database used to run the example systems and methods disclosed herein.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these. As used herein, a phrase referring to "at least one of" or "one or more of" a list of items refers to any combination of those items, including single members. For example, "at least one of: a, b, or c" is intended to cover the possibilities of: a only, b only, c only, a combination of a and b, a combination of a and c, a combination of b and c, and a combination of a and b and c.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising." are intended to imply the inclusion of a stated element or step or group of elements or steps, but not the exclusion of any other element or step or group of elements or steps. Such terms should be interpreted in their most expansive forms so as to afford the applicant the broadest coverage legally permissible. Additionally, various features that are described in this specification in the context of separate implementations also can be implemented in combination in a single implementation. Conversely, various features that are described in the context of a single implementation also can be implemented in multiple implementations separately or in any suitable subcombination. As such, although features may be described above in combination with one another, and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flowchart or flow diagram. However, other operations that are not depicted can be incorporated in the example processes that are schematically illustrated. For example, one or more additional operations can be performed before, after, simultaneously, or between any of the illustrated operations. In some circumstances, multitasking and parallel processing may be advantageous. Moreover, the separation of various system components in the implementations described above should not be understood as requiring such separation in all implementations, and it should be understood that the described program components and systems can generally be integrated together in a single product or packaged into multiple products.

What is claimed is:

1. A system for detecting the presence of an unattended occupant inside a vehicle, the system comprising:
    a geophone vibration sensor configured to continuously sample at a predetermined sampling rate the vibration produced by the vehicle and output a geophone sensor voltage signal;
    a cabin temperature sensor configured to continuously sample at a predetermined sampling rate the temperature within the vehicle and output a temperature sensor signal;
    a cabin carbon dioxide ($CO_2$) sensor configured to continuously sample at a predetermined sampling rate the $CO_2$ levels within the vehicle and output a $CO_2$ sensor signal; and
    a controller disposed in communication with the geophone vibration sensor, the cabin temperature sensor, and the cabin carbon dioxide sensor, wherein the controller is configured to trigger a safety protocol to determine the presence of an unattended occupant when the voltage difference ($\Delta V$) between the exponential moving average of a predetermined number of data points of the geophone sensor voltage signal at time ($t_a$) and at a previous time ($t_{n-1}$) is less than or equal to a predetermined $\Delta V$ threshold.

2. The system of claim 1, wherein the predetermined number of data points of the geophone sensor voltage signal is between 2 and 10.

3. The system of claim 1, wherein the predetermined $\Delta V$ threshold is less than or equal to about 0.1 V.

4. The system of claim 3 further comprising a thermal imaging camera configured to monitor the rear cabin of the vehicle at a predetermined frame rate.

5. The system of claim 4, wherein the predetermined frame rate is about 9 Hz.

6. The system of claim 4, wherein the thermal imaging camera is characterized by a field of view of at least 95 degrees.

7. The system of claim 4 further comprising one or more of a PIR motion sensor or a sound sensor, wherein the PIR motion sensor is configured to continuously sample at a predetermined sampling rate an occupant movement within the vehicle and the sound sensor is configured to continuously sample at a predetermined sampling rate an occupant sound within the vehicle.

8. The system of claim 7, wherein the controller is further configured to turn on the thermal imaging camera or monitor a signal from the PIR motion sensor or monitor a signal from the sound sensor, or a combination thereof, if:
    the temperature sensor signal indicates the cabin temperature to be below about 10° C. or above about 30° C.; or
    the exponential moving average of the $CO_2$ level rate of change calculated using the $CO_2$ sensor signal is at least about 0.2 ppm/s.

9. The system of claim 1, wherein the predetermined sampling rate for one or more of the geophone sensor or temperature sensor is about 10 Hz.

10. The system of claim 1, wherein the predetermined sampling rate for the $CO_2$ sensor is about 0.2 Hz.

11. The system of claim 4, wherein the controller is further configured to communicate with a remote server to capture and process one or more of the geophone vibration sensor voltage signal, the temperature sensor signal, the $CO_2$ sensor signal, or a plurality of images captured using the thermal imaging camera.

12. The system of claim 6, wherein the system is further configured to communicate with an app installed on a car owner's mobile device.

13. A system for detecting the presence of an unattended occupant inside a vehicle, the detection system comprising:
- a transponder unit comprising a plurality of sensors configured to monitor environmental conditions inside the vehicle; and
- a receiver unit disposed in bidirectional data communication with the transponder unit, the receiver unit comprising:
  - a geophone vibration sensor configured to continuously sample at a predetermined sampling rate the vibration produced by the vehicle and output a geophone sensor voltage signal; and
  - a controller, wherein the controller is configured to trigger a safety protocol if the voltage difference ($\Delta V$) between the exponential moving average of a predetermined number of data points of the geophone sensor voltage signal at time ($t_a$) and at a previous time ($t_{n-1}$) is less than or equal to a predetermined $\Delta V$ threshold.

14. The system of claim 13, wherein the predetermined number of data points of the geophone sensor voltage signal is between 2 and 10.

15. The system of claim 13, wherein the predetermined $\Delta V$ threshold is less than or equal to about 0.1 V.

16. The system of claim 13, wherein the plurality of sensors in the transponder unit comprises one or more of a temperature sensor, a $CO_2$ sensor, a PIR motion sensor, or a sound sensor.

17. The system of claim 16, wherein the transponder further comprises a thermal imaging camera.

18. The system of claim 13, wherein the transponder unit is configured to be removably disposed in one or more of a ceiling of the vehicle or a grab handle disposed above a rear seat of the vehicle.

19. The system of claim 13, wherein the transponder unit further comprises a rechargeable battery.

20. The system of claim 13, wherein the receiver unit further comprises a rechargeable battery.

21. The system of claim 13, wherein the transponder unit and receiver unit are configured to wirelessly communicate with each other.

* * * * *